United States Patent [19]

Florin et al.

[11] Patent Number: 5,792,667
[45] Date of Patent: Aug. 11, 1998

[54] PROCESS AND A DEVICE FOR THE DETECTION OF SURFACE PLASMONS

[76] Inventors: Ernst-Ludwig Florin, St.-Rita-Weg 19, 82041 Oberhaching; Hermann Gaub, Akilindastrasse 5, 82166 Graefelfing, both of Germany

[21] Appl. No.: 491,866

[22] PCT Filed: Dec. 23, 1993

[86] PCT No.: PCT/EP93/03678

§ 371 Date: Aug. 15, 1995

§ 102(e) Date: Aug. 15, 1995

[87] PCT Pub. No.: WO94/15196

PCT Pub. Date: Jul. 7, 1994

[30] Foreign Application Priority Data

Dec. 24, 1992 [DE] Germany ............... 42 44 086.6

[51] Int. Cl.$^6$ ..................... G01N 21/00; G01N 25/20
[52] U.S. Cl. ............... 436/147; 422/68.1; 422/82.05; 422/51
[58] Field of Search ............... 422/82.05, 82.12, 422/82.02, 68.1, 51; 436/151, 147, 164; 356/317, 318, 445

[56] References Cited

U.S. PATENT DOCUMENTS

| | | | |
|---|---|---|---|
| 4,889,427 | 12/1989 | VanVeen et al. | 422/82.05 |
| 5,327,225 | 7/1994 | Bender et al. | 422/82.05 |
| 5,415,842 | 5/1995 | Maule | 422/82.05 |
| 5,492,840 | 2/1996 | Malmqvist et al. | 422/82.05 |

FOREIGN PATENT DOCUMENTS

| | | |
|---|---|---|
| 337000 | 9/1983 | Germany. |
| 214140 | 8/1992 | WIPO. |

OTHER PUBLICATIONS

J. Vac. Sci. Technol., vol. 11, No. 6, Nov./Dec. 1974, pp. 1004–1018 (Copyright 1974 by the American Vacuum Society).

Solid State Communications, vol. 56, No. 6, pp. 493–496, 1985.

H. Raether: "Surface Plasma Oscillation and their Applications" from Physics of Thin Films published by G. Hass, M.H. Francobe and R.W. Hoffmann, New York, Wiley, J., 1977, vol. 9:145–261.

Zeitschrift für Physik 216, pp. 398–410, 1968.
Zeitschrift für Naturerforschung 23a, pp. 2135–2136.
Physical Review Letters 21, p. 1530, 1968.
"Proceedings of the SPIE 897" pp. 100–107, 1988.
"Nature 332.14" pp. 615–617, 1988.
Surface Science 137 (1984) pp. 373–383, Benno Rothenhäusler et al., "On the Decay of Plasmon Surface Polaritons at Smooth and Rough Ag–Air Interfaces: A Reflectance and Photo–Acoustic Study".

Applied Physics A. Solids and Surfaces; vo. 48, 1989, Heidelberg DE, pp. 497–500; Y.L. Xie et al. "Bolometric Observation of Nonradiative Decay of Surface Plasmons in Silver". See the whole document.

Applied Optics; vol. 21, No. 5, 1 Mar. 1982, New York, U.S., pp. 949–954; T. Inagaki et al. "Photoacoustic Study of Surface Plasmons in Metals". See the whole document.

Optics Communications; Bd. 91, Nr. 3/4, 15 Jul. 1992, Amsterdam, NL; Seiten 255–259; B. Wang et al. "Photoacoustic Investigation of Surface Plasmons Polaritons in different Ag Interfaces". Siehe das ganze Dokument.

Primary Examiner—Jeffrey Snay
Attorney, Agent, or Firm—Christie, Parker & Hale, LLP

[57] ABSTRACT

The invention relates to a process and device for detecting surface plasmons. According to the invention, the surface plasmons are excited by radiation energy in a thin material layer and, on decaying, release heat producing a temperature rise in the material layer. To simplify the detection of the surface plasmons technically and at the same time especially to attain a good lateral and temporal resolution, an electrothermal sensor allocated to the material layer measures a parameter of the layer in the irradiation region at the same time as the temperature rise and emits a signal corresponding to that parameter. An ultra-thin-film thermometer is, in particular, used to detect the surface plasmons. The process and device are applicable especially to the field of bio and immuno sensory analysis.

42 Claims, 5 Drawing Sheets

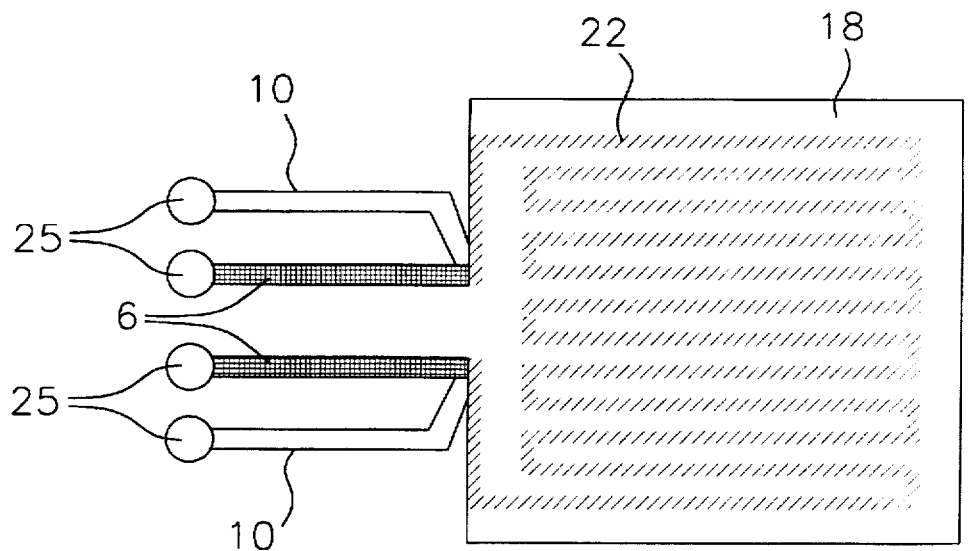
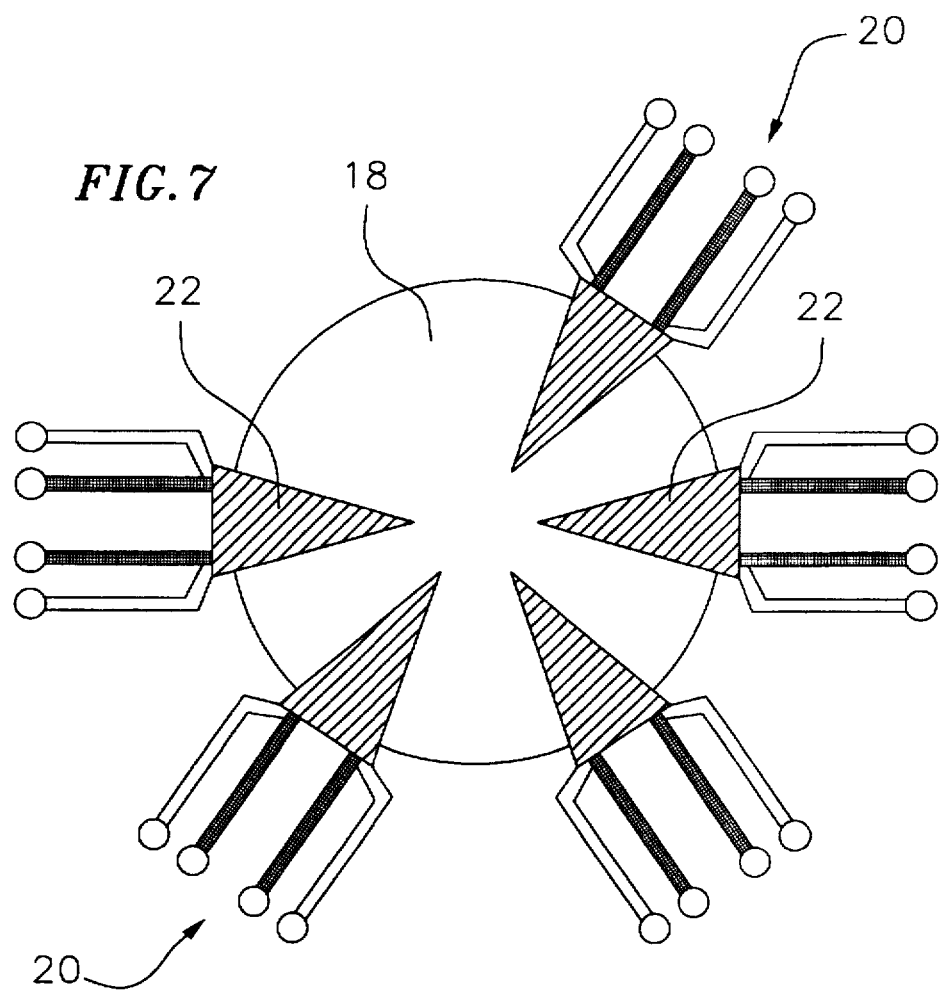

PROCESS AND A DEVICE FOR THE DETECTION OF SURFACE PLASMONS

The invention relates to a process and a device for the detection of surface plasmons, which have the features according to the preamble of claims 1 and 15 and to a thermocouple, in particular for detecting surface plasmons, which has the features of the preamble of claim 36.

The invention serves in particular for detecting surface plasmons. Collective excitations (electron density waves) of an electron gas of a metal or a semiconductor at an interface of metal/dielectric and/or semiconductor/dielectric are designated as surface plasmons. Due to the concentrated localization of the surface plasmons at the interface of metal/dielectric, their properties depend to a very high degree on the physical parameters of the interface. The high sensitivity for surface phenomena is the reasons that surface plasmon spectroscopy has experienced an intensive development both in the scientific field and in sensor technology (e.g. biosensor technology, immunosensor technology).

So far, several principles have been used for exciting or detecting surface plasmons.

The excitation and detection of surface plasmons by means of electron scattering is described in H. Raether: "Surface plasma oscillations and their applications" from "Physics of thin films", published by G. Hass, M. H. Francombe and R. W. Hoffmann, New York, Wiley, J., 1977, vol. 9: 145–261. This method is very complex and is used almost exclusively in the scientific field.

Moreover, surface plasmons are excitable and detectable by light. Light excitation and detection is used both in the scientific field and in sensor technology. The physical properties of the surface plasmons defines a specific setup for excitation and detection by means of optics. In most cases parallel monochromatic p-polarized light is radiated on the interface of metal/dielectric, and the reflected intensity is measured. Energy and pulse preservation, which must be ensured for exciting surface plasmons can be complied with for a specific wavelength of the exciting light only at a specific angle of incidence, the angle of resonance. Consequently, the reflected intensity is plotted against the angle of incidence (plasmon spectrum) to determine the angle of resonance. The angle of resonance is given by the angle of minimum reflectivity. If the optical properties of the interface are changed, this can e.g. be observed by a displacement of the angle of resonance.

A Kretschmann-Raether configuration for surface plasmon spectroscopy is described in Zeitschrift für Naturerforschung 23a, pages 2135 to 2136. This configuration is used most both in science and in sensor technology. The setup with which the surface plasmons can be excited and detected is relatively simple. The light impinges through a prism which is directly in contact with a thin metal and/or semiconductor layer on this layer and excites in it the corresponding surface plasmons. Since the surface plasmons on the surface of the thin layer opposite to the prism are excited, the interface of metal/dielectric is easily accessible to sensor technology in this setup.

An Otto configuration is described in Zeitschrift für Physik 216, pages 398 to 410, 1968, in which a prism is disposed at a distance to a metal film, and surface plasmons are excited in the interface of the metal film facing the prism. This configuration has the disadvantage that the interface of metal/dielectric is no longer freely accessible. Consequently, it is less suited for sensor technology.

A further process for surface plasmon spectroscopy using a grating coupling as known from Physical Review Letters 21, page 1530, 1968, the production of the corresponding optical grating being in particular relatively expensive.

The excitation of the surface plasmons is observed via the reduced reflectivity for the impinging monochromatic, p-polarized light in the three configurations described above. Since the width of the resonance may be about 0.5° if a corresponding metal is used, both the angle of incidence and the angle of reflection must be measured accurately to one hundredth of a degree.

Several processes are known for measuring the reflected intensity as a function of the angle.

The reflected light can e.g. be measured at the angle of reflection by means of a photodiode.

In this method the measured signal is averaged over the area illuminated at the interface. The lateral resolution ability (i.e. the local resolution) is consequently in the magnitude of the beam diameter. It is of advantage here that the lateral resolution ability with a laser customarily used as the light source is in the range of a few millimeters. It is a further disadvantage that the angle of reflection must be measured with very great accuracy.

It is known from "Proceedings of the SPIE 897", pages 100 to 107, 1988, to bundle parallel monochromatic, p-polarized light by means of a lens. The focus of the lens is on the viewed specimen surface. The reflected light cone is detected by means of a camera in locally resolved fashion. The lateral resolution ability is given by the cross-section of the focus (some micrometers) in this method. It is disadvantageous in this detection process that the angle of reflection must again be measured with great accuracy. The use of the camera and an associated computer results in a technically complicated measurement of the reflectivity. It is also disadvantageous that either the focus of the lens must be moved across the interface or the interface itself must be moved to use the basically high lateral resolution. This requires in the first case a scanning means for the impinging light beam and in the second case a controllable precise x-y table.

The principle of the plasmon microscope is known from the magazine "Nature 332.14", pages 615 to 617, 1988. Here, parallel, monochromatic, p-polarized light impinges on the interface. The reflected beam is projected to a video camera by means of an imaging lens. For subsequent evaluation, the image of the interface is transmitted to an electronic image processing. By varying the angle of incidence, a plasmon spectrum can be recorded by means of an image processing with a lateral resolution ability of a few micrometers. The disadvantage of this method is the high technical expenditure due to the imaging optics, camera and image processing system.

Consequently, the invention is based on the object of improving a process and a device of the type mentioned at the beginning to the effect that surface plasmons can be detected in a technically simplified fashion with a good lateral resolution ability.

This object is attained by the characterizing features of claims 1 and 15. Since the physical parameter of the layer of material is measured in the irradiation region, no lateral transport of the heat of decomposition to the electrothermal sensor must be effected. The increase in temperature of the irradiated layer of material, which is caused in the irradiation region is directly ascertained. Accordingly, the signal emitted by the electro-thermal sensor corresponds directly to the temperature of the layer of material. Any change of this temperature can be instantaneously detected so that a measurement by means of the electrothermal sensor is possible with a good temporal resolution. In this fashion, the excitation of the surface plasmons and thus their detection can be implemented in simple fashion by means of a direct picking up of the signal of the sensor. This signal is a measured quantity for the amount of heat released during the decomposition of the surface plasmons. The angle of reflection and its complicated measurement, as necessary in the described prior art, are no longer required. The excitation of the surface plasmons can be carried out by means of one of the described excitation processes.

According to the invention a direct statement on the increase in temperature results from the signal emitted by the sensor. The plasmon resonance and thus the detection of surface plasmons can be carried out directly by means of a corresponding standardization of the sensor.

Thus, it is also of advantage if an evaluation unit determines a plasmon spectrum from the sensor signal as a function of the angle of incidence of the radiation energy relative to the layer of material. The variation of the angle of incidence can e.g. be implemented by pivoting the layer of material with respect to the impinging beam. A measurement of the reflected or transmitted radiation as a function of the angle of reflection and its intensity must no longer be carried out according to the invention. The sensor signal can be determined in the same fashion as a function of the frequency of the radiation energy.

In an advantageous embodiment the electrothermal sensor measures a thermoelectrical effect (e.g. Seebeck effect, Peltier effect) the sensor being composed of a first and a second electric conductor, which overlap each other forming at least one contact point.

The radiation energy is supplied to the layer of material at least in the area of the contact point, the contact point being laterally structured in such fashion that it can be illuminated with a sufficiently high light intensity.

A sensor is known, in which the resistance defined directly by the temperature of the layer of material, is measured.

The layer of material or a part of the layer of material is disposed in the irradiation region, the layer of material being preferably contacted by the resistance sensor outside the irradiation region.

The resistance sensor can be composed of two spaced films of material contacting the thin layer of material at two points. As is generally known, these are connected to a voltage detector for picking up a difference in voltage. It is also possible to connect the resistance sensor in accordance with the 4-point measuring process to a current source via two additional conductive films of material.

The films of material of the resistance sensor, which are connected to the voltage detector, are in direct contact with the thin layer of material, whereas the films of material connected to the current source contact the other films of material adjacent to the thin layer of material. Analogously, a reverse arrangement of the films of material connected to the voltage detector and/or the current source as regards the thin layer of material is possible.

The first and the second film of material, the first film of material being in each case connected to the voltage detector and the second film of material being in each case connected to the current source, are disposed adjacent to the thin layer of material in a side-by-side relationship or one upon the other forming a contact point. The films of material and the thin layer of material can be applied from the same material in one operation, e.g. by means of the customary process of layering technique. On the other hand, the first and second metal films can be applied with a thickness being greater as compared with the layer of material, if their inherent resistances are to be reduced.

The resistance sensor and, from case to case, part of the thin layer of material can be covered by an insulating material in the direction towards the supplied radiation energy and/or on the specimen side.

In this case, the resistance sensor may e.g. be arranged at least partially in the irradiation region without it being possible that the surface plasmons are e.g. directly excited in the resistance sensor.

The current source used for the resistance sensor is as stable as possible and only emits that much current as it is necessary for the detection of the voltage signal by the voltage detector. The voltage detector measures as current-free as possible, a simultaneous measurement of signal shape and phase being possible.

In an advantageous embodiment of the invention a radiation source emits the radiation energy in the form of electro-magnetic radiation. In this connection it is in particular advantageous if the radiation source emits the electro-magnetic radiation in the form of monochromatic p-polarized light. A laser can e.g. be used as the radiation source, the laser light being supplied to the layer of material via a collecting and supplying means as a parallel light.

In a further embodiment of the invention a modulation means such as a chopper modulates the radiation with a defined frequency, and the evaluation unit detects the signal of the sensor in phase-correct fashion. A lock-in amplifier is e.g. used in this case as the evaluation unit.

If a surface plasmon spectrum is to be in particular determined, it is advantageous if the thermocouple measures the increase in temperature due to the decomposition heat of the surface plasmons by means of direct or indirect contact to a surface of the thin layer of material. In the case of an indirect contact a dielectric layer or a heat-insulating layer is e.g. disposed between the layer of material and the thermocouple.

In another embodiment of the invention at least one conductor of the thermocouple forms the thin layer of material. This means that the surface plasmons are directly excited in at least one conductor of the thermocouple and the increase in temperature occurs directly in the thermocouple.

In this connection it results as a further advantage that, if a specimen is applied to at least the layer of material and/or a contact point of the sensor, the sensor detects the surface plasmons modified by the specimen, and the evaluation unit determines a modified plasmon spectrum characteristic of the specimen and a characteristic sensor signal shape. The sensor signal shape permits the making of further statements on heat transport, relaxation behaviour and the like, in particular in the interface, in accordance with the signal amplitude or time behaviour of the signal. In this fashion the sensor can particularly be used for biosensor technology and immunosensor technology. The specimen can be directly contacted with the surface of the layer of material and/or the sensor by means of an associated specimen chamber, the specific properties of the specimen influencing the surface plasmon spectrum and the characteristic properties of the specimen being thus measurable.

In order to simultaneously detect various measured quantities on a limited sensor surface in a simple fashion and to obtain still additional information on the interface and the specimen to be examined at the same time as the measuring of the plasmon resonance, it is furthermore advantageous if the evaluation unit carries out a corresponding number of measurements with a plurality of contact points by means of a simultaneous or sequential reading out of a thermocouple.

Many measurements, in particular also reference measurements, are possible at the same time on a narrowly limited space by means of the side-by side arrangement of several contact points and their simultaneous or sequential readability. Due to this, a two-dimensional detector array is set up according to the invention. The contact points of this array can be specifically modified in view of the magnitudes to be measured. In addition to a specific effect in the direct proximity, a reference measurement can in particular be carried out by means of a further contact point. This makes it e.g. in biosensor technology possible to differentiate the specific protein bond from the non-specific one at a surface.

An arrangement of the resistance elements and/or resistance sensors being analogous to the arrangement of a plurality of thermocouples described above is also possible. A plurality of resistance sensors with an allocated layer of material may be arranged sequentially in a specimen chamber containing a specimen. If the specimen flows e.g. in longitudinal direction through the specimen chamber, a linear arrangement of the thin layers of material with allocated resistance sensors (sensor array) is especially well suited for flow measurements, changes of the specimen in terms of time being e.g. measurable.

Analogously, a plurality of thin layers of material may be arranged in a specimen chamber along a circumference of a circular specimen chamber, the resistance sensors projecting radially outwards from the specimen chamber. A plurality of measurements on a relatively small space are possible in this example of embodiment.

If in this connection the resistance sensor and partly a part of the thin layer of material is covered by an insulating material in the direction towards the supplied radiation energy and/or towards the specimen, the entire upper half-space may be covered by the specimen chamber as regards the resistance sensor covered by the insulating material.

In a further example of a resistance sensor the thin layer of material is arranged e.g. in a meander-shaped fashion between the contact points to the resistance sensor, whereby a relative great length of the thin layer of material results. In this fashion a greater temperature effect results and thus a facilitated measuring of the resistance.

In the process and/or device according to the invention the thin layer of material in which surface plasmons are excited by one of the aforementioned standard processes is consequently replaced with two different metals, semiconductors or conductive alloys in such fashion that the two metal films form an ultra-thin film thermocouple, and the thermoelectric voltage between the two metals can e.g. be measured. The film thickness is between 50 and 600 Å, preferably between 200 and 400 Å. The thickness of the film is selected in such fashion that optimum conditions for exciting the surface plasmons are given at the contact point of the two films. The contact point is laterally structured in such fashion that it can be illuminated with a sufficiently high light intensity.

Since the thermoelectric voltage generated by the decomposition heat of the surface plasmons at the contact point is largely independent of the surface of the contact point, it may be optionally reduced. This applies at least to the area in which the electron gas can be considered as free in lateral expansion. The lateral resolution ability results from the size of the contact point. The contact point has preferably a surface of=1 mm².

The films of the sensor may be applied in simple fashion onto a substrate by means of corresponding masks. This process corresponds to the application of various layers in semiconductor element production, the application being e.g. carried out by means of vapor-deposition or the like. Due to the direct application of the sensor onto the substrate, it can be exchanged easily together with the substrate. The substrate and also the device, in particular the collecting and supplying means etc. must comply with specific known conditions in order to be able to excite surface plasmons in the layer of material. Such conditions apply e.g. to refractive indices, the permeability with respect to electromagnetic radiation or the like.

In one embodiment of the invention the collecting and supplying means is formed by at least one prism or one cylindrical lens. It is furthermore of advantage if the substrate with sensor is applied onto the prism and/or the cylindrical lens with a suited immersion oil. The use of a suited immersion oil provides an unproblematical connection between the exchangeable substrate with sensor and the fixed optical components such as prism or cylindrical lens.

The invention also relates to a thermocouple, in particular for detecting surface plasmons. Thermocouples in thin-film technology are known, with which temperatures can be measured at the smallest bodies with a good local and temporal resolution. The film thickness of the thermocouples is a few μm and more.

These known thin-film thermocouples are not suited in particular for measuring the decomposition heat of surface plasmons with a sufficiently good local and temporal resolution, since the decomposition heat of the surface plasmons at the interface of metal/dielectric is emitted in the range of a few nanometers. According to the invention at least one conductive film with a film thickness of only 50 Å (5 nm) to 600 Å (60 nm) is formed. This film thickness results in a sufficient magnitude of the electric conductivity within the films.

Such a thermocouple may also only have one conductive film, which is e.g. applied onto a bulk material as a second conductor and an insulator. A contact point for measuring the thermoelectrical effect is formed in the overlapping area of the two conductors. Both conductors may also be applied onto a common substrates as conductive films.

If gold and silver are selected as metals for the films, film thicknesses of a few nanometers are sufficient.

As described above, one or several of these thermocouples (ultrathin film thermocouples) and/or resistance sensors can be applied onto one and the same substrate. The lateral structuring necessary for this can be achieved by means of a thermal vapor deposition through a mask. The contact points of the various films and/or thin layers of material are that close to each other that, if the thermocouples and/or resistance sensors are used for the detection of surface plasmon according to the process and/or device described above, surface plasmons can be excited at the same time in all thermocouples and/or all thin layers of material by means of the impinging light. The ultra-thin film thermocouples may either be independent on one and the same substrate, i.e. each thermocouple consists of a pair of conductors which is electrically insulated from the other, or the thermocouples are connected in such fashion by a common conductor that the thermoelectrical voltage can be picked up at various points by means of the respective other conductor. The spacing of the individual thermocouples and/or thin layers of material is basically determined by the lateral decomposition length of the surface plasmons and can at least be reduced up to the μm range. It is also possible to combine thermocouples and resistance sensors with each other within one specimen chamber.

If the invention is used in biosensor technology, an improved vertical resolution ability of the surface plasmon spectroscopy results by the use of the combination of silver/gold film as compared with the pure gold film frequently used in biosensor technology. The gold surface is chemically preserved with respect to the applied specimen. The specimen is applied onto the contact point and/or the thin layer of material. A gas, a liquid, a solid film or the like may be used as a specimen. The contact point/layer of material is modified for the respective specimen in such fashion that only the respectively relevant magnitude is measured such as the concentration of a specific protein in a solution, the presence of a specific antibody or antigen in a solution, the concentration of a specific gas or of a liquid, changes in the state of aggregation of a substance or the like. Due to the size and the shape of the measuring signal of the sensor standardized to the impinging power density of the radiation energy, additional information on the interface of metal/dielectric can be obtained, which has not been accessible by means of the former processes.

In addition to the use of surface plasmon spectroscopy, the invention and in particular the thermocouple can be used for the highly sensitive measurement of the surface temperature.

Advantageous examples of embodiments of the inventions will be explained and described in greater detail in the following by means of the FIGS. enclosed in the drawing.

FIG. 6 shows a further example for a resistance sensor, and

FIG. 7 shows an example of embodiment of a sensor array.

Figure 1:
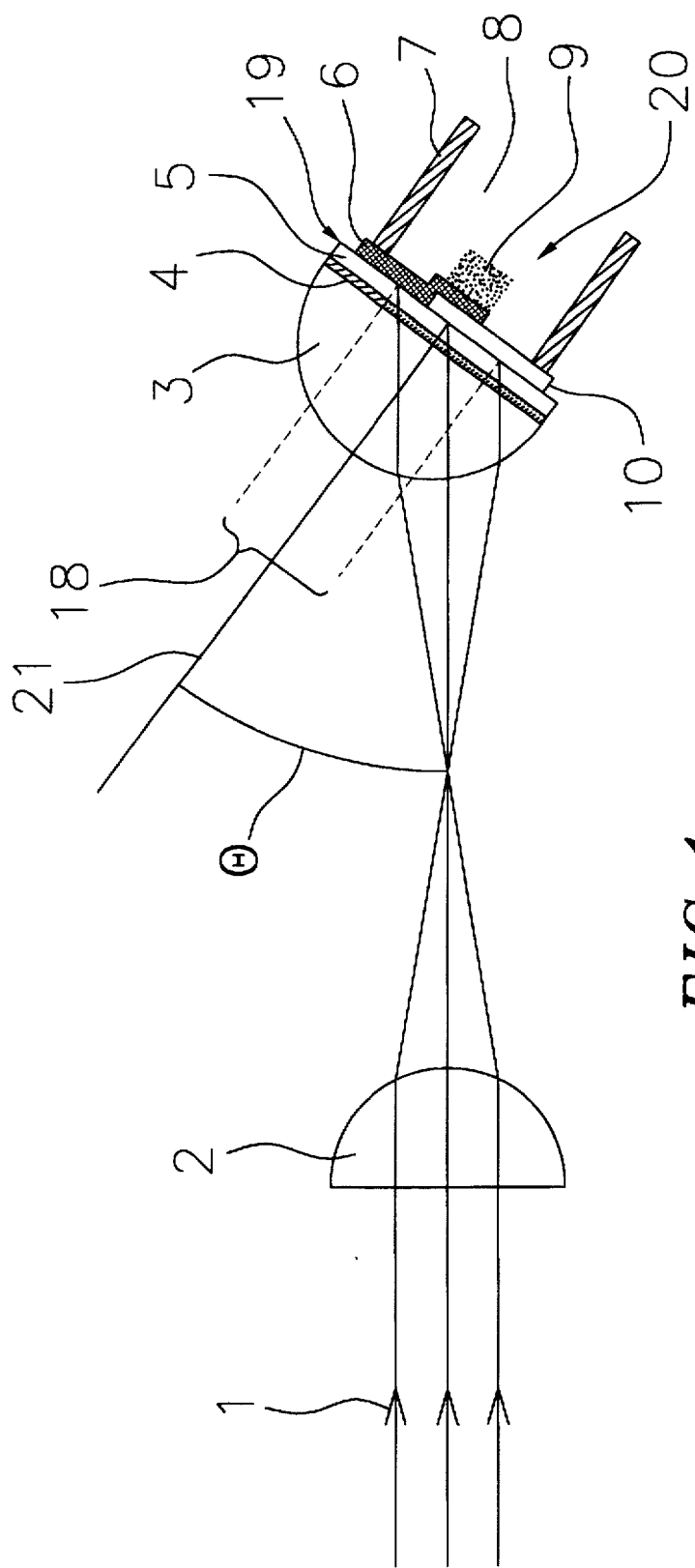
FIG. 1 shows a lateral sectional view of an embodiment of the invention.

An embodiment of a device for carrying out the process according to the invention is represented in FIG. 1. A parallel light bundle 1 can be supplied to a substrate/sensor unit 19 as a parallel light beam via a collecting and supplying means 2, 3. The light beams may in particular be unpolarized, circularly polarized or unpolarized. A central region 18 of the unit 19 is illuminated. The light beams impinge on the substrate/sensor unit 19 at an angle of incidence of θ with respect to a mid-perpendicular 21.

The substrate/sensor unit 19 comprises a substrate or specimen holder 5 and a sensor 20. The sensor 20 is applied onto one side of the specimen holder 5. The opposite side of the specimen holder is optically connected to a cylindrical lens 3 of the supplying and collecting means 2, 3 by means of an immersion liquid 4. The light beams 1 are supplied to the cylindrical lens 3 by a second cylindrical lens 2 of the supplying and collecting means.

The sensor 20 is formed by two metal films 6 and 10 which overlap each other in the central area of the substrate/sensor unit 19. The overlapping area forms a contact point 16 for measuring thermoelectrical voltage or thermoelectric current. The metal film 6 is made of pure gold, and the metal film 10 is made of pure silver. Doped gold and/or silver films may also be used. The contact point 16 of the two layers forms an effect-specific sensor surface area 9 by means of which specimens contained in a specimen medium 8 are detectable. The specimen medium 8 is contained in a specimen chamber 7 which is disposed on the side of the sensor 20 facing the substrate 5.

The irradiation region 18 illuminated by the light beams 1 is disposed substantially symmetrically to the mid-perpendicular 21, the contact area of the two metal films being particularly illuminated.

Figure 2:
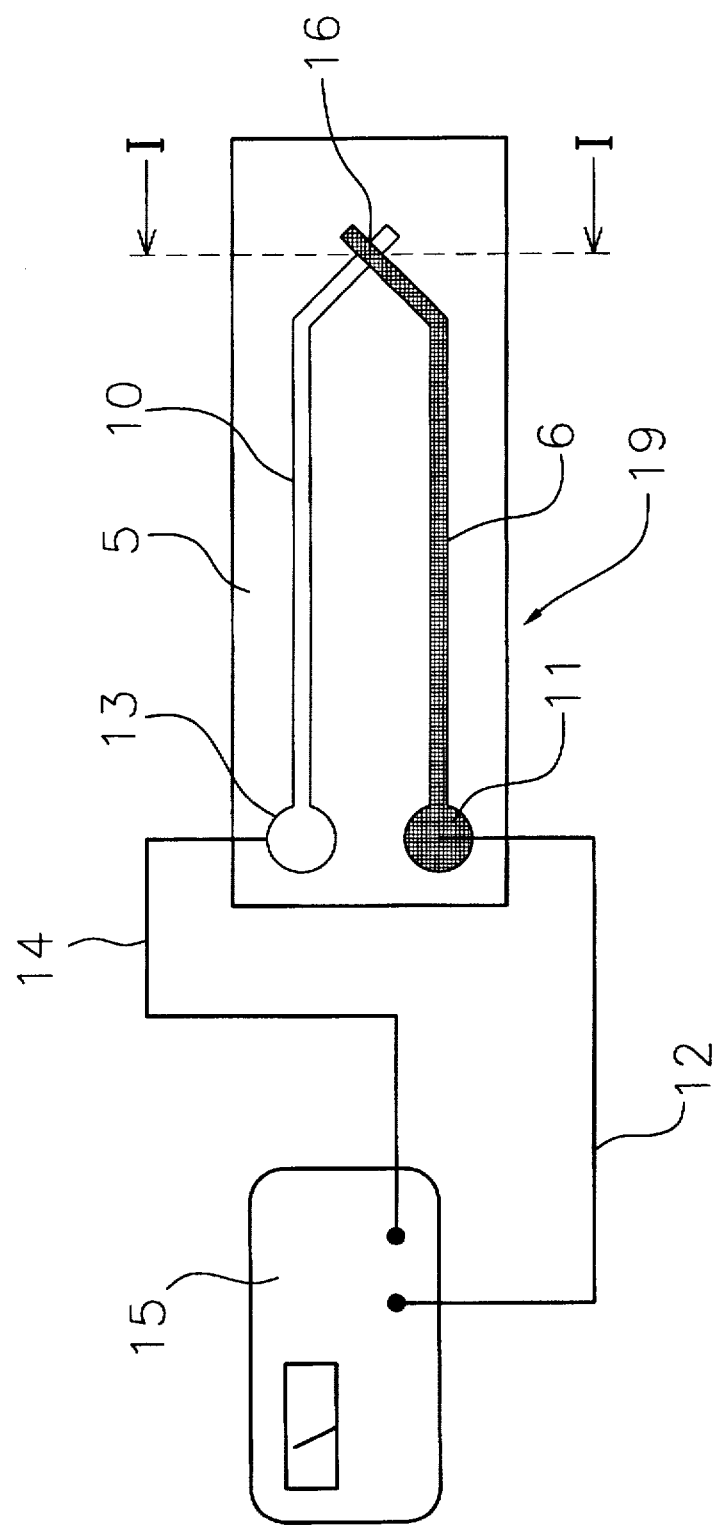
FIG. 2 shows a top view of the embodiment according to FIG. 1, FIG. 1 corresponding to a section along line I—I.

The embodiment according to the invention according to FIG. 1 is represented as a top view in FIG. 2. The object holder 5 has a substantially rectangular shape. The metal films 6 and 10 extend substantially in parallel to the longer sides of the object holder 5. A substantially circular connection point 11 and/or 13 is formed at one end of each metal film. At their opposite ends the metal films converge at an angle of about 45° in bent fashion and form the contact point 16 in an overlapping area. Both metal films 6 and 10 extend slightly beyond the contact point 16.

The representation according to FIG. 1 corresponds to a section along line I—I of FIG. 2.

Copper connections 12 and 14 are connected at the connection points 11 and 13. They establish a connection to an evaluation unit 15. The thermoelectrical voltage measured by the thermocouple according to the invention or a corresponding thermoelectrical current can be recorded and evaluated by means of it.

The evaluation unit 15 is either formed by a voltage measuring device or a lock-in amplifier. If a lock-in amplifier is used, a corresponding modulation of the impinging light intensity is e.g. generated by means of a chopper. The voltage measuring device can be built up in simple fashion from an operation amplifier circuit. This operation amplifiers should only have a very small drift and a very small offset. If several connections of different thermocouples are to be measured, it can be switched over between them by means of a measuring point selector.

Figure 3:
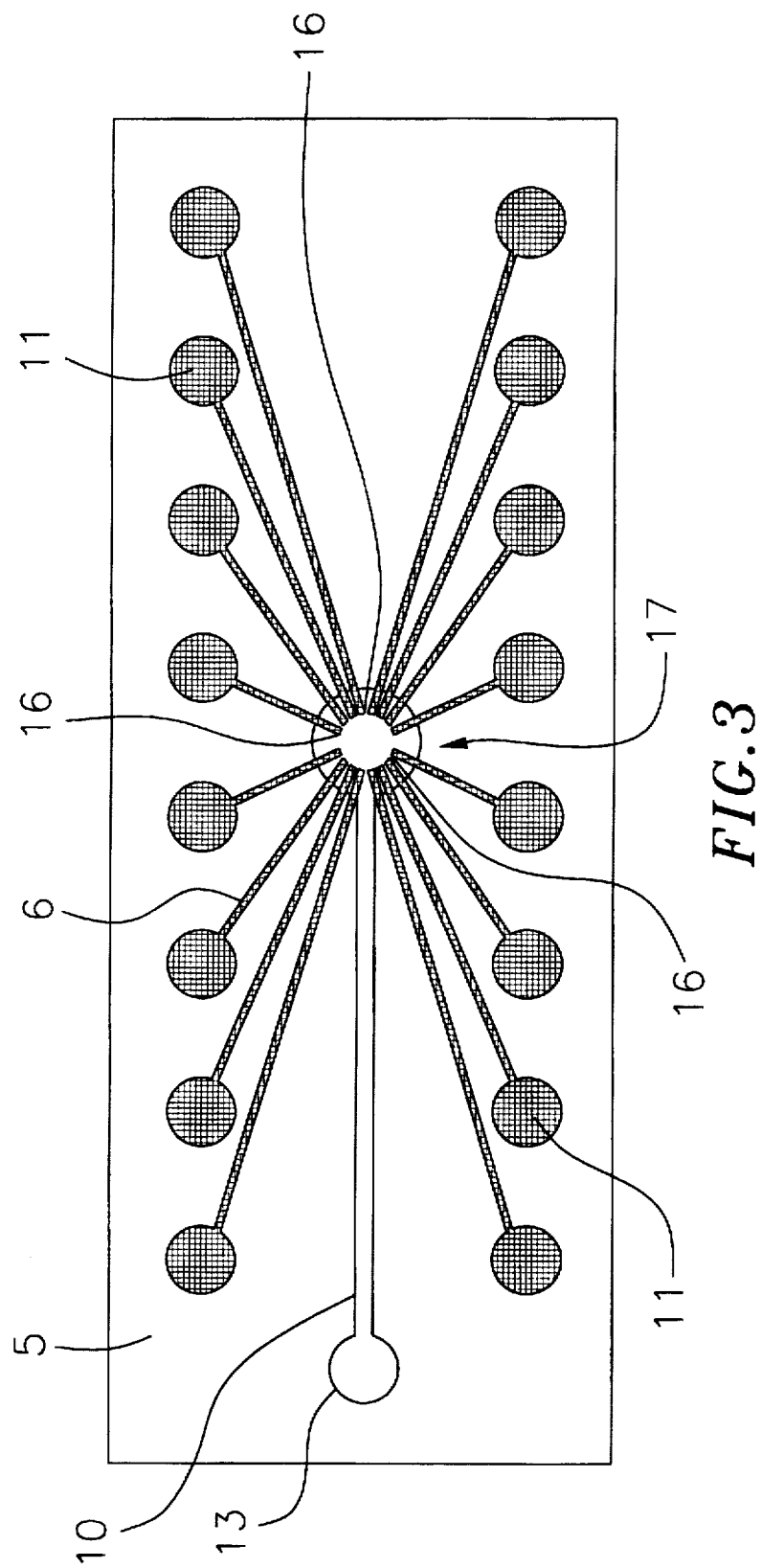
FIG. 3 shows a top view of a further example of embodiment of the invention.

Another embodiment of the invention is represented in FIG. 3. A number of metal films 6 are applied onto an object holder 5 in this embodiment. They are disposed with respectively one end on a common, substantially circular connection surface 17 of the other metal film 10. The overlapping areas of the metal films 6 with the metal film 10 on the connection surface 17 form a plurality of contact points 16. They are disposed in spaced relationship along the circumference of the connection surface 17.

The metal films 6 have corresponding connection points 11 at their opposite ends, which are connected to the evaluation unit 15 according to FIG. 2 via copper connections. The connection point 13 of the metal film 10 is correspondingly connected to the evaluation unit 15.

The production and the use of the device and/or the thermocouple according to the invention will be briefly described in the following.

In a first working step the metal film 10, e.g. highly pure silver, is applied onto the specimen holder 5 with a corresponding thickness, e.g. 250 Å, and a corresponding geometry through a mask. In a second step the metal film 6, e.g. highly pure gold, is also applied with a corresponding thickness, e.g. 250 Å, and corresponding a geometry. The application can e.g. be carried out by means of thermal evaporation in a vacuum vapor deposition system. Both metal films are applied in such fashion that they only have one contact point 16, which has e.g. a surface of about 0.5 mm².

The two metal films may of course also be supplied onto the substrate in reverse order. In this case, the contact points are covered upwards by the connection surface 17, in particular in the embodiment according to FIG. 3.

The lines 12 and 14 are connected to the metal films 6 and 10 at the connection points 11 and 13. The lines are selected so that contact voltages being as small as possible occur both at the connection points 11 and 13 and at the contact points to the evaluation unit. The lines may e.g. be made of pure copper.

Figure 4:
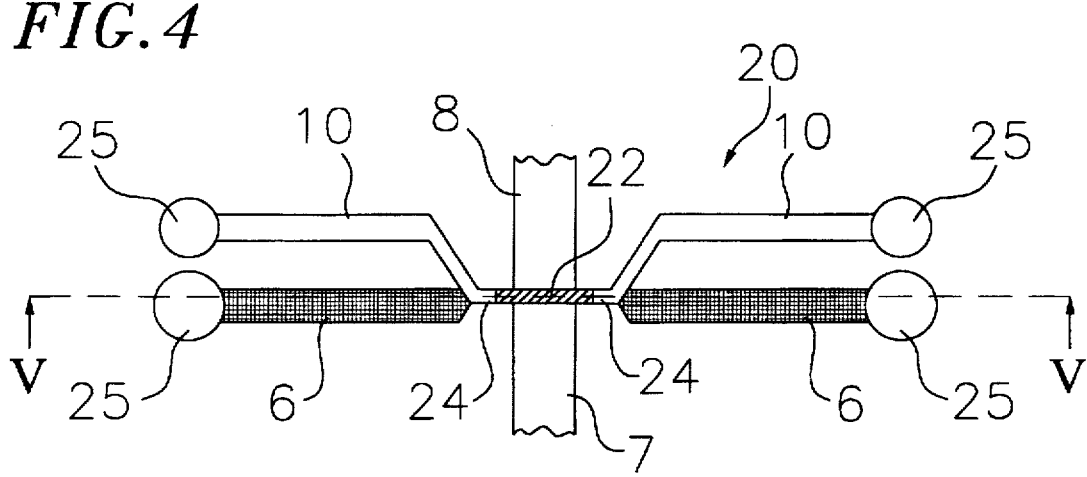
FIG. 4 shows a top view of a resistance sensor.

A resistance sensor and/or a resistance element 20 for temperature-dependent resistance measurement is represented in FIG. 4. It is formed by respectively 2 conductive films of material 6, 10 laterally to the thin layer of material 22. The films of material 10 are e.g. connected to a voltage detector (not shown) and the films of material 6 are connected to a current source (not shown). Circular connection contacts 25 are disposed at the ends of the films of material 6 and/or 10 facing the thin layer of material 22. The resistance sensor 20 is connected to the voltage detector and the current source and/or an evaluation unit 15 according to FIG. 2 via the same.

The current-carrying films of material 6 contact the substantially rectangular layer of material at their shorter rectangle sides. The films of material 10 for voltage detection extend in the direction towards the film of material 6 at their end allocated to the layer of material 22 and contact the same from above in the contact areas 24.

A specimen chamber 7 extends substantially across the width of the thin layer of material 22 between the contact areas 24, where a corresponding specimen 8 is in contact with the layer of material 22 within the specimen chamber.

If the sample chamber 7 extends vertically to the layer of material 22 across a corresponding length, a plurality of resistance sensors 20 can e.g. be disposed in the longitudinal direction of the specimen chamber with associated layer of material 22. In this fashion, a specimen 8 flowing in longitudinal direction through the specimen chamber 7 is e.g. measurable at different points in the direction of flow.

Figure 5:
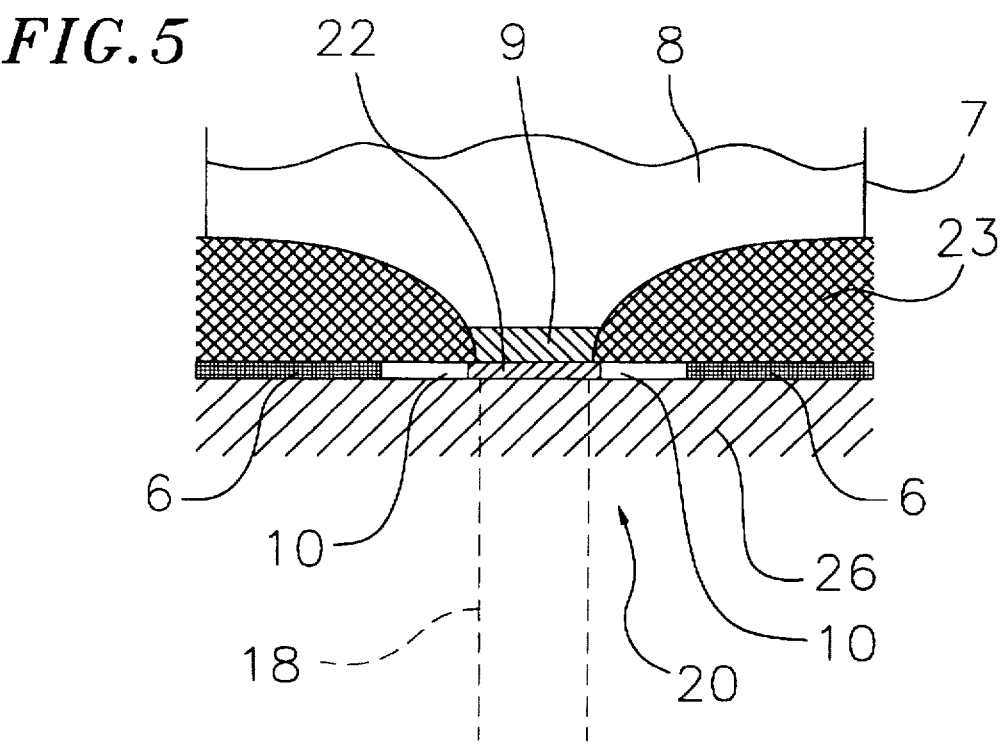
FIG. 5 shows a section along line V—V of FIG. 4.

A section along line V—V of FIG. 4 is shown in FIG. 5. As opposed to FIG. 4, an insulating material 23 is additionally applied onto the resistance sensor 20. It covers at least those areas of the films of material 6 and 10 which are disposed adjacent to the layer of material 22. In this fashion, the specimen chamber 7 and thus the sample 8 can substantially expand in the entire upper half-space above the insulating material 23. The radiation area 18 may also extend up to the insulating material 23.

As opposed to the example represented in FIG. 4, the films of material 6 and 10 are disposed with the same thickness and in a side-by-side relationship on a substrate 26, the layer of material 22 and the films of material 6 and 10 having the same thickness. Moreover, as opposed to FIG. 4, the film of material 10 contacts the layer of material 22 laterally in FIG. 5, whereas the film of material 6 contacts the film of material 10. As for the rest, the arrangement of the films of material 6 and 10 is as shown in FIG. 4.

The resistance sensor 20 is disposed on one side of a specimen chamber 7 or a radiation area 18 in FIG. 6. Identical reference numerals characterize identical parts and will not be mentioned again.

As opposed to the examples of the resistance sensor described so far, the layer of material 22 is disposed in meander-like fashion, an end of the layer of material being in contact with a pair of films of material 6, 10 and the other end being in contact with another pair of films of material 6, 10.

A circular specimen chamber 7 or a circular radiation area 18 is shown in FIG. 7. A plurality of resistance elements 20 is disposed in spaced relationship along the circumference of the specimen chamber 7 and/or the radiation range 18. The thin layer of material 22 allocated to each resistance sensor 20 is substantially triangular, the resistance sensor 20 being in contact with the hypotenuse of the triangle and the triangle vertex pointing substantially towards the center of the specimen chamber 7 and/or the irradiation region 18.

In the examples represented in FIGS. 6 and 7, the specimen chamber 7 can naturally have a shape deviating from that of the irradiation region 18.

Moreover, the films of material for the resistance sensors may be produced of a material identical to that of the layer of material or the materials described above for the thermocouple. Films of material and the layer of material may be produced in the same or a different thickness.

The optical components of the invention, i.e. the collecting and supplying means are adjusted in such fashion with respect to each other that a monochromatic, p-polarized light beam 1 impinges in parallel at an exactly defined angle of incidence θ with sufficiently high power density on the contact point 16 and at least illuminates the same completely. The thermoelectrical voltage and/or the thermoelectrical current between the metal films 6 and 10 is picked up at the lines 12 and 14 by means of the evaluation unit. The thermoelectrical voltage is proportional to an increase in temperature generated by the decomposition heat by the surface plasmons excited by the p-polarized light. A complete resonance curve of the surface plasmons is obtained if the amount of the difference of the thermoelectrical voltage between, on the one hand, the illuminated contact point 16 and, on the other, the unilluminated contact point 16 is plotted against the angle of incidence in the area of the surface plasmon excitation. The detected signal corresponds to the increase in temperature at the contact point, which is achieved due to the decomposition heat of the surface plasmons and a general absorption.

Since surface plasmon can only be excited with p-polarized light, the general absorption can be determined by means of a measurement with s-polarized light. Due to a standardization of the thermocouple, i.e. the indication of a change in voltage per degree Celsius, the temperature at the interface can be determined. A quasi-stationary equilibrium temperature is measured at the contact point 16 in the metal films with this method.

If the specimen to be measured in the specimen medium 8 is applied onto the contact point and/or the layer of material 22, the surface plasmons react at the interface to the sample in very sensitive fashion to the changed physical parameters of the interface. The change in these parameters can be detected by means of a change in the surface plasmon spectrum.

We claim:

1. A process for detecting surface plasmons which are excited in a thin layer of material by a radiation energy supplied through an irradiation region of the layer of material and which emit decomposition heat causing an increase in temperature in the layer of material upon their decomposition, the process including providing an electrothermal sensor comprising a thermocouple coupled to the layer of material for directly measuring the temperature of the layer of material in the irradiation region and for emitting a signal corresponding to the increase in temperature.

2. A process according to claim 1, characterized in that an evaluation unit (15) determines a plasmon spectrum in the thin layer of material from the signal as a function of an angle of incidence θ of the radiation energy relative to the layer of material (6, 22) or as a function of the frequency of the radiation energy.

3. A process according to claim 2, characterized in that a specimen is applied onto the layer of material or onto at least one contact point of the sensor, the sensor detects the surface plasmons modified by the specimen and the evaluation unit determines a modified plasmon spectrum characteristic of the specimen and measures a characteristic sensor signal shape.

4. A process according to claim 3, characterized in that electrothermal sensors measure locally the increase in temperature caused by the decomposition heat of the surface plasmons at a plurality of points within a specimen chamber containing the specimen.

5. A process according to claim 2, characterized in that a radiation source emits the radiation energy in the form of electromagnetic radiation.

6. A process according to claim 5, characterized in that the radiation source emits electromagnetic radiation (1) in the form of monochromatic, p-polarized light.

7. A process according to claim 6, characterized in that a collecting and supplying means supplies the light as a parallel light to the layer of material.

8. A process according to claim 2 wherein the electro-thermal sensor measures a thermoelectrical effect.

9. A process according to claim 8, wherein the electro-thermal sensor comprises first and second conductors, juxtaposed to define at least one contact point and wherein the thermoelectrical effect is measured at said at least one contact point of said first and second conductors.

10. A process according to claim 9, characterized in that a modulation means modulates the radiation with a defined frequency and the evaluation unit detects the signal of the sensor in phase-correct fashion.

11. A process according to claim 9 characterized in that the sensor measures the increase in temperature by means of a direct or indirect contact with a surface of the thin layer of material.

12. A process according to claim 11, characterized in that the thin layer of material forms at least one conductor of the sensor.

13. A process according to claim 9, wherein said sensor includes a plurality of contact points characterized in that the evaluation unit carries out a corresponding number of measurements, including reference measurements, by means of a simultaneous or sequential reading out of said sensor with said plurality of contact points.

14. A process according to claims 13, characterized in that a modulation means modulates the radiation with a defined frequency and the evaluation unit detects the signal of the sensor in phase-correct fashion.

15. A process according to claim 9, characterized in that the radiation energy is supplied at least in said contact point of the first and second conductors.

16. A process according to claim 15 characterized in that the sensor measures the increase in temperature by means of a direct or indirect contact with a surface of the thin layer of material.

17. A process according to claim 15, characterized in that a radiation source emits the radiation energy in the form of electromagnetic radiation.

18. A device for carrying out the process according to claim 1, which comprises a thin layer of material capable of producing surface plasmons responsive to a radiation energy which emit decomposition heat causing an increase in temperature in the layer of material upon their decomposition, a radiation source for emitting electromagentic radiation, a collecting and supplying means for generating a parallel radiation from the electromagnetic radiation, and for supplying said parallel radiation to the thin layer of material in its irradiation region for exciting surface plasmons, characterized in that at least one sensor measuring the increase in temperature is allocated to the thin layer of material.

19. A device according to claim 18, characterized in that the radiation source emits monochromatic, P-polarized light.

20. A device according to claim 18, characterized in that the collecting and supplying means has a cylindrical lens or a prism.

21. A device according to claim 20, characterized in that the radiation source emits monochromatic, p-polarized light.

22. A device according to claim 18, characterized in that the sensor (20) is designed as a thermocouple with a first (6) and a second (10) conductive film of material, which overlap each other forming at least one contact point (16).

23. A device according to claim 22, characterized in that at least the first conductive film (6) forms the thin layer of material.

24. A device according to claim 23, characterized in that the thermocouple is applied onto a substrate.

25. A device according to claim 23, characterized in that the conductive films are made of metal, a semiconductor or a conductive alloy.

26. A device according to claim 25, characterized in that the layer of material and the first and second conductive films of material have the same thickness and are formed from the same material.

27. A device according to claim 25, characterized in that the films have a thickness of less than 500 Å.

28. A device according to claim 27, characterized in that the first film is made of gold and the second film is made of silver.

29. A device according to claim 27, characterized in that the film thickness is 50 to 300 Å.

30. A device according to claim 29, characterized in that the first film is made of gold and the second film is made of silver.

31. A device according to claim 30, characterized in that the gold and silver are present in pure form or doped.

32. An device according to claim 22, characterized in that the thermocouple is applied onto a substrate.

33. A device according to claim 32, characterized in that the substrate forms an exchangeable unit together with the thermocouple.

34. A device according to claim 32, characterized in that an immersion liquid is disposed between the collecting and supplying means and the substrate.

35. A device according to claim 32, characterized in that a plurality of thermocouples (20) are applied onto the substrate (5).

36. A device according to claim 35, characterized in that the conductive films of the thermocouple can be applied onto the substrate using corresponding masks.

37. A device according to claim 35, characterized in that the thermocouples are connected to an evaluation unit.

38. A device according to claim 37, characterized in that the connection between thermocouples and the evaluation unit (15) is effected by copper, silver or gold connections (12, 14).

39. A device according to claim 35, characterized in that the thermocouples (20) have a common conductor (10) and a plurality of individual conductors (6).

40. A device according to claim 39, characterized in that the respective contact point of each of the thermocouples is disposed within the range irradiated by the electromagnetic radiation.

41. A device according to at least one of claims claim 40, characterized in that a specimen to be measured is applied onto at least one contact point of the thermocouple.

42. A device according to claim 41, characterized in that the thermocouples are connected to an evaluation unit.

* * * * *

UNITED STATES PATENT AND TRADEMARK OFFICE
CERTIFICATE OF CORRECTION

PATENT NO. : 5,792,667
DATED : August 11, 1998
INVENTOR(S) : Ernst-Ludwig Florin; Hermann Gaub It is certified that error appears in the above-identified patent and that said Letters Patent is hereby corrected as shown below:

On the title page,

Item [76] Inventors, after "Ernst-Ludwig Florin" delete
"St-Rita-Weg 19, 82041 Oberhaching" and insert therefor
-- Kirchwald 21, 69251 Gailberg --.
Column 1, line 17, change "reasons" to -- reason --.
Column 5, line 61, change "of=1 mm$^2$" to -- of =1 mm$^2$ --.
Column 6, line 37, after "onto" delete "a".
Column 7, lines 20,21, change "inventions" to -- inventions --.
Column 7, line 22, change "drawing" to -- drawings --.
Column 7, line 39, change "unpolarized" to -- p-polarized --.
Column 8, line 23, change "This" to -- Thus --.
Column 11, line 31, change "plurity" to -- plurality --.
Column 11, line 65, change "P-polarized" to -- p-polarized --.
Column 12, line 32, change "An device" to -- A device --.
Column 12, line 59, after "according to" delete "at least one of claims".

Signed and Sealed this

Twenty-sixth Day of October, 1999

Attest:

Q. TODD DICKINSON

*Attesting Officer*    *Acting Commissioner of Patents and Trademarks*